United States Patent [19]

Andreotti et al.

[11] Patent Number: 5,082,628
[45] Date of Patent: Jan. 21, 1992

[54] LUMINOMETER

[75] Inventors: Peter E. Andreotti, Lauderhill; Irwin S. Morse, Miami; Jerry T. Thornthwaite, Miami; Malcolm L. Heimer, Miami; Jorge D. Salinger, Miami; Joseph J. Sobodowski, Miami, all of Fla.

[73] Assignee: Park Pharmaceuticals, Inc., Miami, Fla.

[21] Appl. No.: 409,108

[22] Filed: Sep. 19, 1989

[51] Int. Cl.⁵ .................. G01N 21/00; G01N 21/76
[52] U.S. Cl. ......................... 422/82.08; 422/82.05; 422/52; 436/172; 435/808; 356/434; 356/440
[58] Field of Search .......... 422/82.05, 82.08, 52; 436/172, 809; 356/434, 436, 440; 435/808

[56] References Cited

U.S. PATENT DOCUMENTS

| | | | |
|---|---|---|---|
| 4,115,010 | 9/1978 | McAleer et al. | 356/440 |
| 4,431,307 | 2/1984 | Suovaniemi | 356/440 |
| 4,472,352 | 9/1984 | Quesneau et al. | 435/808 |
| 4,563,331 | 1/1986 | Losee et al. | 435/808 |
| 4,730,921 | 3/1988 | Klein et al. | 356/440 |
| 4,755,055 | 7/1988 | Johnson et al. | 422/52 |
| 4,772,453 | 9/1988 | Lisenbee | 422/73 |
| 4,818,883 | 4/1989 | Anderson et al. | 422/52 |
| 4,826,660 | 5/1989 | Smith et al. | 422/82.08 |

FOREIGN PATENT DOCUMENTS

| | | | |
|---|---|---|---|
| 0217632 | 4/1987 | European Pat. Off. | 436/809 |
| 0257048 | 11/1987 | Japan | 356/440 |
| 2211607 | 7/1989 | United Kingdom | 436/172 |

*Primary Examiner*—Robert J. Warden
*Assistant Examiner*—Theresa A. Trembley
*Attorney, Agent, or Firm*—Fidelman & Wolffe

[57] ABSTRACT

A luminometer for assaying bioluminescence and chemiluminescence reactions characterized by sample wells having transparent bottom walls, a light detector positioned beneath the sample wells and a reagent injector above the wells.

7 Claims, 3 Drawing Sheets

LUMINOMETER

This invention relates to a novel luminometer and in particular to a luminometer which employs luminescence to perform a series of analytical tests rapidly.

BACKGROUND OF THE INVENTION

For some years prior to the date hereof the art has appreciated that luminescence reactions, particularly bioluminescence and chemiluminescence reactions can be the basis for extraordinarily sensitive analytical assays or tests. Such assays can, for example, combine the specificity of an immunoassay with the detection limits for measurements of light. For instance, luminescent immunoassays are comparable in sensitivity to radioimmunoassays and offer the significant advantages of freedom from radioactive reagents.

However, as of date hereof the potential for rapid accurate assays offered by bioluminescence and chemiluminescence reactions has not been achieved. To some extent, perhaps to a great extent, the analytical luminometer instruments offered to the art heretofore are ill-suited to rapid processing of numerous samples in luminescence reactions assays. Certainly, they have not met with widespread acceptance. This invention relates to an improved luminometer instrument for conduct of luminescence, (i.e., bioluminescence or chemiluminescence) assays.

RATIONALE OF THE INVENTION

An attribute desired as much in a luminometer as in any analytical instrument is the capability to analyze a great number of similar samples one by one, quickly and accurately. Improved sensitivity is, of course, desired.

These objectives have been achieved by the luminometer of this invention.

In the luminometer of this invention a large number of samples placed in a sample holder that comprises a modified microtiter plate are introduced into the luminometer instrument at one time, then measured, one by one in some sequence until the entire batch of samples on the sample holder has been analyzed.

The well known microtiter plate which typically contains wells in 8 rows and 12 columns, namely, 96 wells, each of about 0.25–0.30 ml capacity, is a conveniently sized sample holder. Moreover, microtiter plates are small enough so that several, e.g., three modified microtiter plates, can fit into a luminometer of convenient size for an analytical laboratory. Thus, 96 samples in triplicate or the near to 300 individual samples in the wells of three modified microtiter plates sample holders may be assayed in a single batch.

It goes without saying that the large number of samples that may be placed into one or more of the sample holder plates will not be assayed simultaneously (by some luminescence reaction). They may, in fact, be assayed one at a time; conceivably only one light detector and one inlet tube for adding necessary reagent(s) to each sample need be in the luminometer. Preferred practice of this invention, however, is to provide a light detector and reagent feed tube(s) for each sample holder plate. Preferred is three plates, three light detectors, etc., in the luminometer. The plates are spaced apart so measurements made of luminescence on one plate will not interfere with measurements on the other plates.

Accordingly, necessary components in the luminometer of this invention are a movable table on which the sample holder plate(s) are removably mounted, an X, Y movement mechanism which generates closely controlled movement of the table repetitively accurate to about 0.0015 inch or better, at least one sample holder plate, and a light detector adjacent to and associated with the sample holder plate. Each sample (well) in the sample holder plate is brought into line of sight registry with the light detector in some predetermined sequence. Also necessary is one or more inlets in an appropriate registry with the light detector for luminescence assay to introduce reagent(s) needed for the luminescence reaction into each sample in turn Luminometers systems such as are discussed above have been suggested to the art as, for example, by U.S. Pat. No. 4,772,453 and by EPO publication 0025350 published Mar. 18, 1981.

The present invention is directed to an improved luminometer system.

THE INVENTION

For further understanding of the present invention reference is made to the attached drawing illustrating a preferred mode of the invention and wherein.

Figure 4:
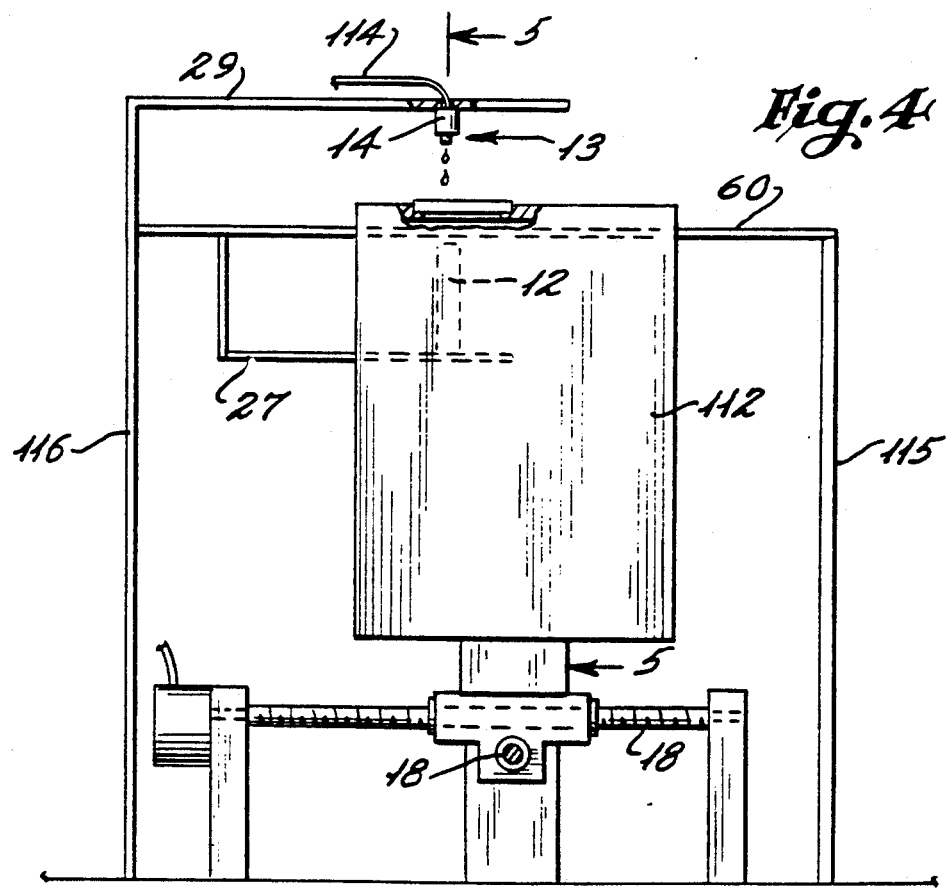
FIG. 4 is a side section through the luminometer.
Figure 5:
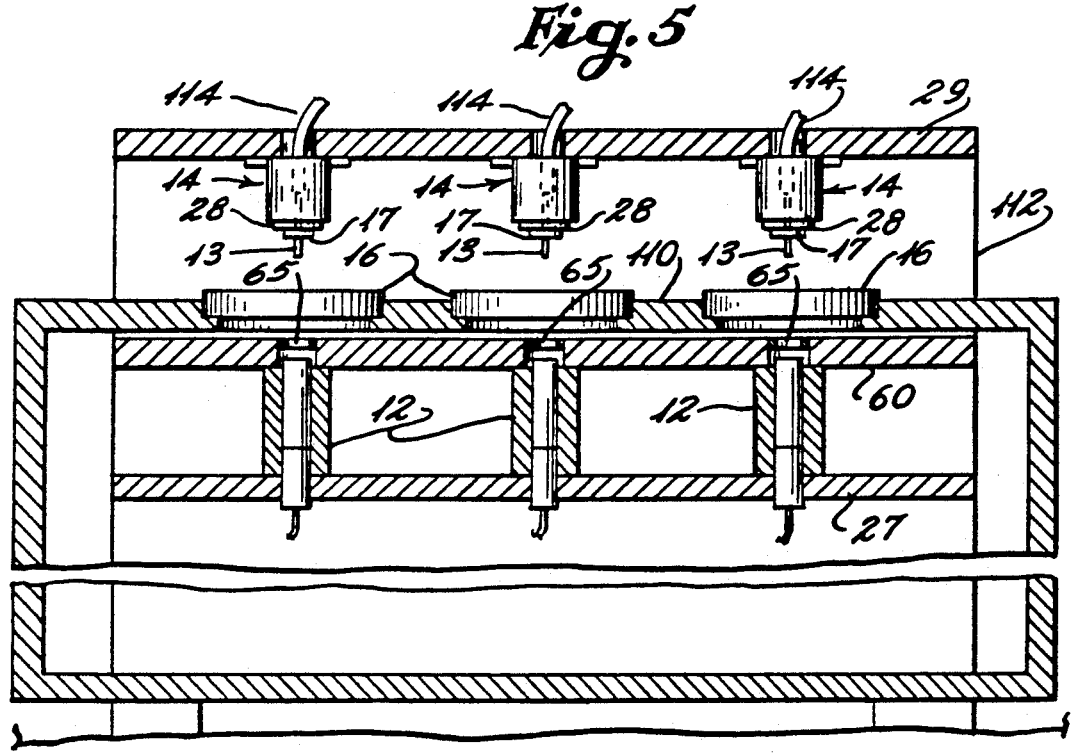
FIG. 5 is a front view section through the luminometer at the location of line 5—5 on FIG. 4.

Referring now to the drawing and, in particular to FIG. 4 and FIG. 5 whereon is shown luminometer 5 containing the components which comprise the luminescence assay system of this invention, namely, sample holder 16, a light sensor 12 beneath sample holder 16 on a line of sight to one sample at a time, the sensor in the instance of this invention preferably being a state of the art photo multiplier tube, e.g., Hamamatsu R647-04 and an injector 14 above the sample holder for introducing the reagent(s) which generate(s) the desired luminescence reaction in the liquid sample. Needed also is a read out means (not shown) that reports the level and/or quantity of luminescence measured by photomultiplier tube 12. Read out means for photomultipliers are state-of-the-art systems.

In the luminometer read out employed as of the date hereof, the signal pulses from the photomultiplier tube have been amplified, then passed through a discriminator circuit (to distinguish noise from signal) and thereafter counted over the preselected assay test time interval. After subtraction of the background count levels, the net pulse count (or some fraction or multiple there as appropriate) was reported as the raw data of the luminescence assay, usually to a computer for a later conversion into a (printed out) spread sheet report on all of the samples in a batch. The circuitry and other components for this and like read out means are known in the art forming, per se, no part of this invention.

The luminometer of the present invention provides for assaying, one by one, the numerous samples, e.g., 96 that can be placed in the multiplicity of sample wells 30 in sample holder plate 16, (see FIG. 6) preferably in a batch of three such sample holder plates 16 as is illustrated in FIG. 5.

Figure 2:
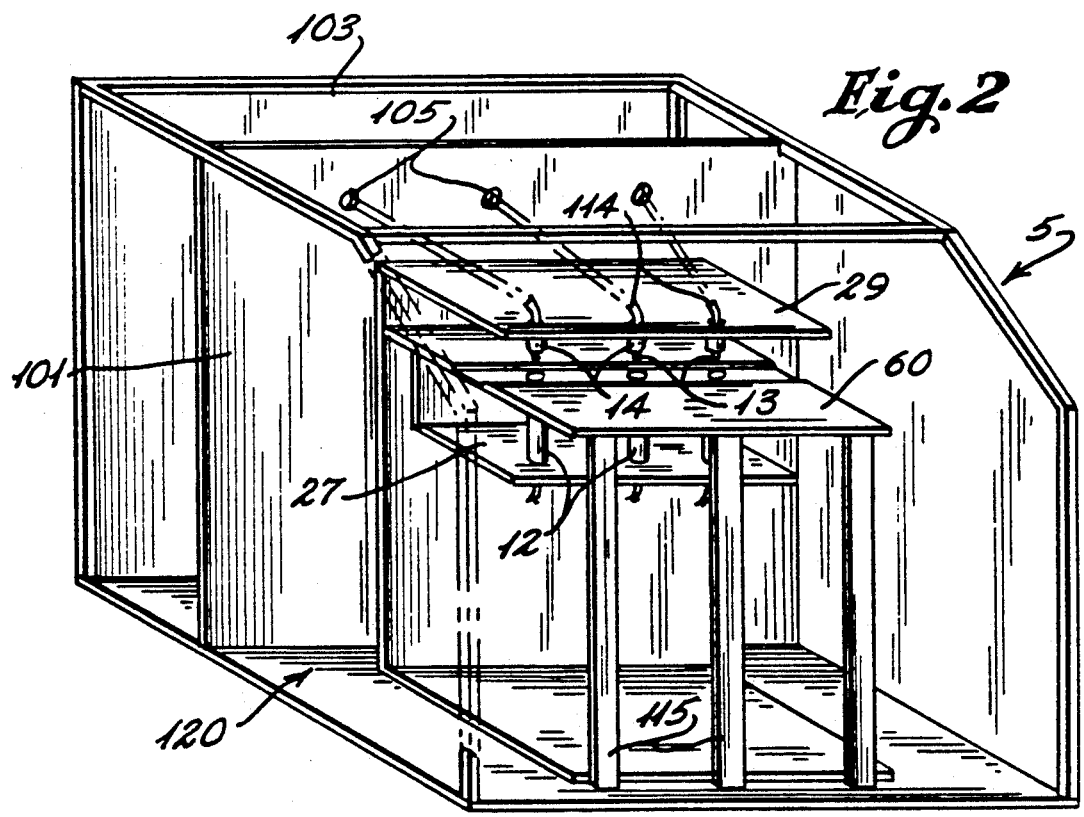
FIG. 2 is a diagrammatic view of the luminometer with the housing and moving parts removed showing the mountings for the light detector and reagent injector.
Figure 3:
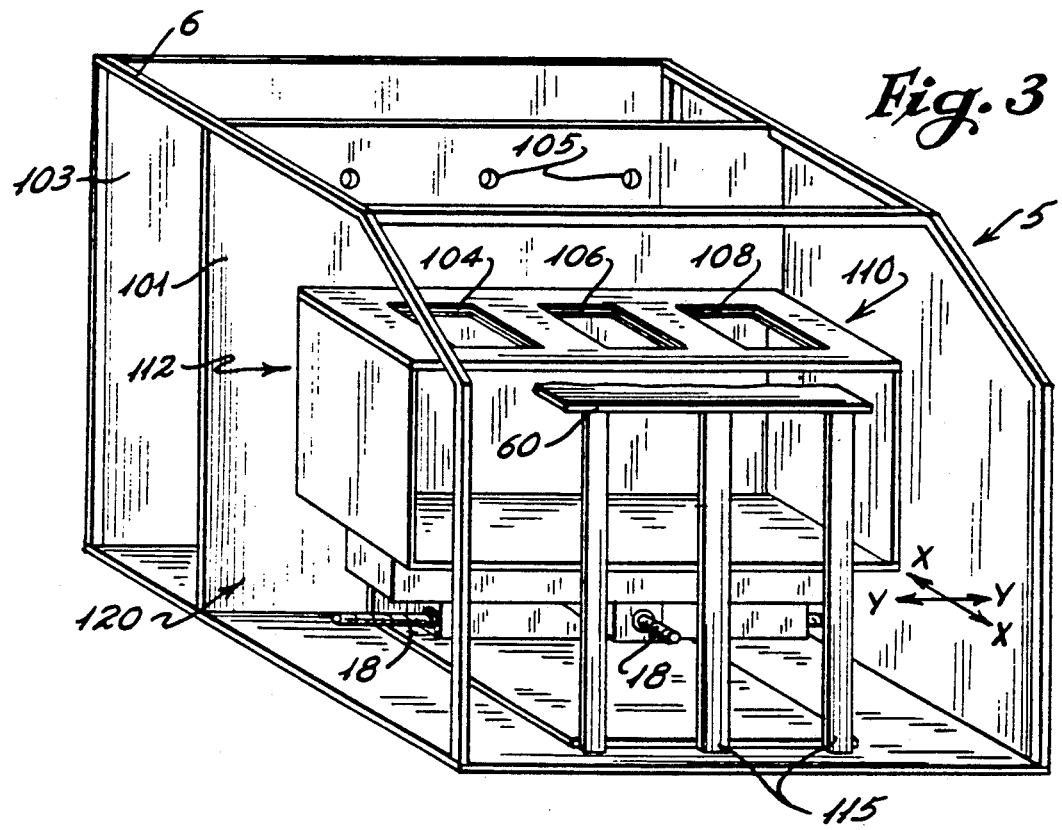
FIG. 3 is a diagrammatic view of the luminometer with the housing and some parts removed, showing the X-Y mechanism and movable table.

Referring now to FIGS. 2, 3 and 4, it may be seen there that the sample holder plate(s) 16 are removably mounted on a table 110 that is movable relative to the stationary photo multiplier tube(s) 12 positioned below table 110 and the injector 14 positioned above Table 110. An X-Y drive mechanism 18, of which many are known to the art and, therefore, is not illustrated, being shown fragmentarily in FIGS. 3 and 4 shifts table 110 relative to the photomultiplier tube (PMT) 12 and injector 14 so that each sample well on the sample holder plate(s) will come into registry with the PMT and also with injector 14 one by one. To repeat, in the luminometer of this invention PMT 12 and injector 14 are stationary.

Although the foregoing discussion speaks of the table being movable, and PMT and injector being stationary, it should be appreciated that the movable/stationary relationship applies only with regard to lateral movement (e.g., in the plane of the table) by the table. Indeed, vertical (upward) movement by injector 14 and/or vertical (downward) movement by PMT 12 may be desired to provide room for insertion of sample holder plate 165 on Table 110.

As may be seen best in FIGS. 3 and 4, Table 110 forms part of a movable chassis 112 that is linked to the X-Y mechanism 18 for controlled movement by the X-Y mechanism. Movable chassis 112 is inside of a stationary cage 116, whereon is mounted the injectors 14 and the PMT 12 above and below Table 110 respectively. Injectors 14 are shown as mounted on an upper shelf 29 on cage 115. The PMT 12 are shown as seated on a lower shelf 27. Between the shelves 27, 29, and beneath Table 110 is a baffle plate 60. The baffle plate 60 is shown as extending to legs 115, which supports may be made part of the front face of the housing 100. Legs 115 are removed for access to X-Y mechanism 18 and to chassis 112 when, as and if maintenance becomes necessary. Conveniently, the luminometer 5 is constructed with a frame 6 around which the sheet metal housing 100 is draped.

Figure 1:
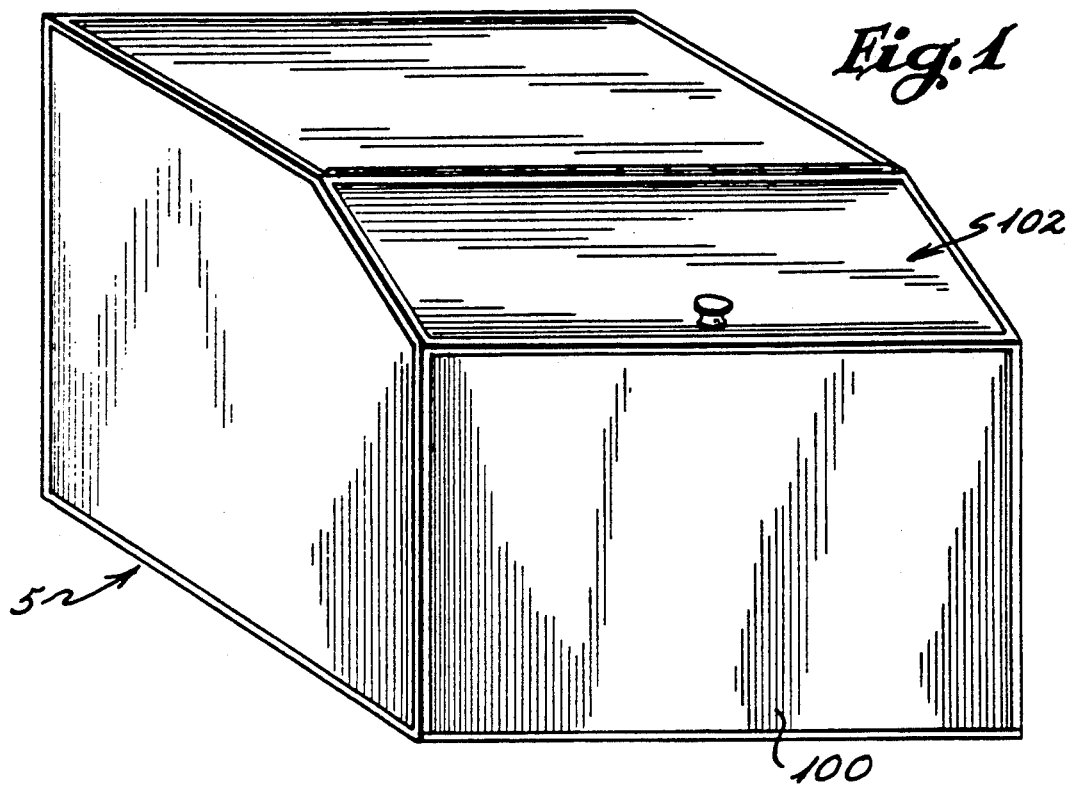
FIG. 1 is a diagrammatic view of the luminometer housing.

Reverting now to FIGS. 1-3 of the drawing it may be seen there that access to the inside of luminometer housing 100 for placement and removal of the sample holder plates therein, is through pivotal movement of a hatch 102 from a light tight closed position to an open position. When hatch 102 is open, sample holder plates each with a multiplicity of samples in the sample wells 30 may be placed (by hand) into the three recesses 104, 106, 108 provided in table 110 for this purpose and, of course, already assayed plates in any of the recesses are removed then.

Desirably an internal well 101 is provided inside housing 100, generating thereby a front compartment 120 containing chassis 112, etc., and rear compartment 103 wherein may be placed all ancillary equipment, e.g., electrical controls, and reagent supply vessels for injectors 14, etc. A reagent supply tube 114 passes from behind internal wall 101 through a port 105 to the injector 14.

In the luminometer of this invention, the reagent injector 14 normally is positioned above the microtiter plate in line with PMT 12. If desired for some luminescence assays injector 14 may be offset (e.g., by one sample). The offset for reagent injector 14 is contemplated for instances where a delay between addition of the reagent and the assay measurement of the resulting luminescence reaction is desired. The offset then is placement of injector 14 at the sample that next will be in line with the PMT or the next succeeding sample, as appropriate. All such locations for injector 14 are considered to be in registry with the PMT. In the mode illustrated, only one reagent injector 14 is present for each sample holder and that injector is in line with the PMT 12 as is indicated on FIGS. 2 and 4. For assays where more than one reagent may be needed, multiple injector nozzles, as necessary will, of course, be present and their placement will be determined by the intended luminescence reaction.

Figure 6:
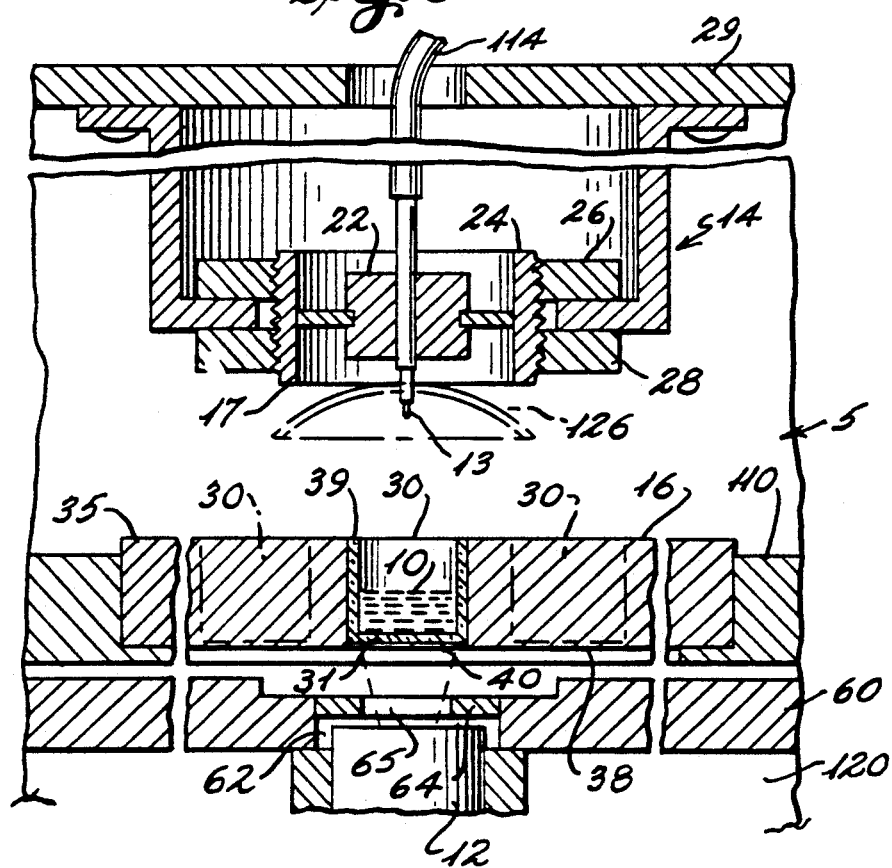
FIG. 6 is an enlarged partial section corresponding to FIG. 5, showing a sample well on the sample holder plate.

Referring now to FIGS. 5 and 6, it may be seen there that injector 14 comprises an assembly wherein a nozzle tip 13 is mounted on the nozzle mounting fixture 17 located on upper shelf 29. Fixture 17 comprises a plug 22 through which the nozzle tip 13 passes and within which the nozzle tip 13 is firmly retained. In turn, the plug 22 is secured in a threaded nut 24. Nut 24 is threaded to upper and lower gaskets 26 and 28 which together lock gaskets and plug to a depending lip or flange on shelf 29.

Each sample well 30 on sample holder plate 16 is provided with a transparent bottom wall 31 so that light generated by the luminescence reaction can pass through (the face of PMT 12. Light from all other sources is avoided. As will be explained hereinafter, several important geometric features are provided in the luminometer of this invention to eliminate impingement of unintended light upon the photo sensitive face of PMT 12.

As already has been pointed out, each sample 10 is disposed inside of a well 30, one of many such wells, e.g., ninety-six in the sample holder plate 16. To repeat, the sample holder plate 16 may be considered to be modified microtiter plate. Like typical microtiter plates the sample holder plate 16 employed with the luminometer of this invention contains a dozen columns numbered 1-12 and 8 rows numbered A-H for a total of ninety-six wells (all as is present in known in the art microtiter plates). The outside dimensions of the plate, the well diameter and well center to center spacing may be the same as in conventional microtiter plates, e.g., the clear molded polystyrene Cell Well TM plate from Corning Glass Works. This mimicry is advantageous since considerable ancillary equipment has been engineered for use with microtiter plates and, therefore, reliable pipetting and control equipment is commercially available for use with the sample holder plates of this invention (e.g., Cavro Instruments) to add, remove, or transfer solution(s) to and/or from up to 12 wells simultaneously on demand. Thus, conceivably the (modified microtiter plate) sample holder plate of this invention could be employed as a microtiter plate, but, of course, the known in the art microtiter plates are not adapted to practice of this invention.

The body 35 of sample holder plate 16 should be opaque, preferably being black. The wells 30 comprise cup shaped inserts with transparent bottoms which are pressed into pass through cylindrical apertures 39 in body 35. The entire well 30 may be transparent or alternatively the side wall of well 30 may be light reflective. However, it is necessary to practice of this invention for the bottom wall 31 of each well 30 to be transparent.

A feature of importance to practice of this invention is that transparent bottom wall 31 of each well 30 is spaced inward from the (planar) lower surface 38 of the sample holder plate body 35. A small but distinct (cylindrical) recess 40 has thereby been created beneath each well 30.

Thus, the drawing, notably FIGS. 5 and 6 illustrates a preferred mode wherein the sample holder plate 16 comprises a black molded body 35 member having therein cylindrical pass through apertures 39 set in the column and row array present as in microtiter plates. Each aperture 39 is plugged by cup shaped well 30 with transparent walls. The well 30 seats in the aperture 39 with its top opening flush to the upper surface of plate body 35 but its transparent planar bottom wall 31 recessed above the bottom surface 38 of the molded plate body 35.

The absolute dimensions of the sample holder plate 16, of the well 30 and of the recess 40 are not critical to practice the invention, although, to repeat, it is advantageous for plate 16 to have the same dimensions as a typical microtiter plate. A sample volume of about 0.25 ml is convenient for luminescence assay purposes. Exemplary dimensions for plate 16 are 1.5 cm for the depth of the plate body 35, about 1 mm for the (depth of) recess 40, an internal diameter of about 6 mm, and a depth of 1.3 cm for well 30. More generally, the depth of recess 40 may vary from 0.5-1.0 mm.

Known in the art photo multiplier tube(s) (PMT) 12, e.g., Hamamatsu R647-04 and read out means such as has been described above are employed in the luminometer 5. Front compartment 120 in housing 100 wherein the PMT 12 are disposed is a light tight compartment. Hatch or lid 102 must fit securely. Thus, PMT 12 is exposed to light only through viewing aperture(s) 65 in the baffle plate 60 provided for this purpose as may be seen in FIG. 5, and FIG. 6.

The PMT 12 is disposed beneath the upper surface of (stationary) baffle plate 60, desirably inside of a cylindrical cutaway 62. The baffle plate 60 is opaque and desirably is black.

An annular focussing collar 64 for the PMT face is disposed in cutaway 62 (above the PMT) face leaving an iris passageway 65 that constitutes the viewing aperture through which light from sample 10 strikes the photo sensitive face of PMT 12. Preferably, the diameter of iris 65 is somewhat less than the diameter of sample well 30, being for example from 0.5-3.0 mm less in diameter. The focussing collar 64 is, of course, opaque, and preferably is black.

It should be appreciated that wells 30 are small and are close together, for example, a particular well 30 being illustrated in FIG. 6 at two-three times full size; for clarity of illustration the next adjacent wells to that illustrated in full are shown by FIG. 6 only in shadow form.

Careful construction of the luminometer as a whole and of the component parts therein is needed. For one thing a reasonable clearance above and below table 110 (and the sample holder plates thereon) must be provided to allow for the movement of table 110 that brings each well of the microtiter plate into registry with PMT 12 and injector 14 in the desired succession but more than enough clearance is not desirable.

As has already been pointed out, the injector 14 must be in its own registry with PMT 12, e.g., injector tip 13 in line of sight with PMT 12 so as to feed reagent directly into the sample 10 in the particular well 30 on line of sight to PMT 12, for readings on rapid onset reactions.

The X-Y movement mechanism must move the table 110 exactly the distance center to center between (adjacent) sample wells, to an accuracy of ±0.0015 or about 0.04 mm. A like level of uniformity in the sample holder plates is important. The distance center to center of each well and within each microtiter plate should be the same in all of the plates. Any deviation in movement or plate structure that positions some sample well 30 significantly off-center from line of sight to the PMT 12 causes some light from the luminescence reaction emitted from sample 10 and passing through transparent bottom 31 to become lost for striking the baffle 60 or the focussing collar 64 instead of the PMT face. Since this luminescence never reaches the PMT 12 to be counted, such loss of emitted light generates reading error.

When Iris 65 is smaller in diameter than well 30 as is illustrated in FIG. 6, and such is preferred, then not all of the light passing through the transparent bottom 31 from a properly centered well 30 will strike the PMT face. In short, light from the annular peripheral edges of transparent bottom 31 is supposed to become lost. As a result, small inaccuracies in centering, either by the X-Y table and/or through minor (off center) irregularities in the sample holder plate, e.g., the ±0.04 mm alluded to above will not generate reading error, until and unless the deviation from strict concentricity of the line of sight well 30 with PMT 12 exceeds the narrowed view path formed by aperture 65 in the iris. To repeat, an iris aperture 65 of diameter smaller than the internal diameter of well 30 is preferred.

As an aside, it is noteworthy that the home position of Table 110, the position to which X, Y mechanism 18 retreats at the end of a batch and/or hatch 102 is opened, extends Table 110 and the plates 16 thereon toward the front face of housing 100 for best access to plates 16.

Placement of sample holder plates 16 into a close fitting space on Table 110 beneath shelf 29 is not difficult. The sample holder plates are small enough for easy manipulation. The luminometer 5 is a conveniently sized unit being, for example, about 15 by 18 by 20 inches.

Some special advantages of the luminometer of this invention over like prior art devices may be made apparent by the following discussion of how the above-described components in the luminometer interact.

Self-evidently, the opaque preferably black members, i.e., sample holder plate body 35, PMT baffle 60 and focussing collar 64, serve to shield the photo sensitive face of PMT 12 from direct and reflected light. The recess 40 beneath well 30 is intended to prevent diffusion of emitted light from any well 30 in a lateral direction.

A direct line of sight path for transmission of luminescence generated in sample 10 to PMT 12 is provided by the transparent bottom 31 of each sample well 30 through the iris 65 of the focussing collar 64. No other potential light source has such a direct path. However, prevention of any and all light leakage to the PMT face is important for best sensitivity and accuracy of the luminometer 5. Thus, if hatch 102 and/or the housing 100 itself is not completely light-tight, serious reading errors will be introduced. It is important also that afterglow light from adjacent wells (out of line of sight) should be precluded from striking PMT 12. Afterglow light, sometimes preglow light as well is present. The usual luminescence reactions used for assay purposes generates light for a finite period of time and the generation of light which is not an instantaneous on-off system increases to a peak level then declines and ceases.

If the luminescence assays are carried out in reasonably rapid succession, more than one sample well 30 might well be emitting light while an assay is under way. Of course, conduct of each successive assay might be delayed until full extinction of the afterglow from all previous assay measurements had occurred but a lengthy time lapse between successive luminescence tests is not desirable. Conduct of assays in rapid succession is preferred. In consequence, the structure of the luminometer of this invention as a whole and of sample holder plate 16 as well is adapted to allow only light from the line of sight sample well 30 to reach the PMT face, preventing afterglow and/or preglow luminescence light from reaching the photosensitive PMT face.

Since a direct path for transmission of light to the PMT face is allowed only from the bottom of the sample well containing the sample being assayed, light from all other wells can reach the PMT face only through reflection. Use of opaque light absorbent materials used for plate body 35, for baffle plate 60, and for collar 64 reduces reflection of light. Mention has already been made that in preferred practice, the plate body 35, the PMT baffle and the focussing collar are black (to better absorb incident light). The inside face(s) of hatch 102 and of housing 100 also may be black.

The clearance distances above table 110 between the top of sample holder plate(s) 16 and stationary shelf 29 and the clearance beneath bottom of sample holder plate(s) 16 and the stationary baffle plate 60 are made as small as possible. The recessed location sample wells 30 and of the PMT face as discussed above reduce further reduces light leakage to the PMT face.

Provision of the recess 40 beneath each sample well 30 and location of the PMT face beneath the focussing collar 64 behind the iris eliminate any line of sight passage to PMT 12 from all sample wells, save from the one line of sight well 30 being assayed. Thus, afterglow from any other well 30 is never in any line of sight with the PMT face, even most obliquely. Afterglow light is directed down onto baffle 60 and obliquely from the well 30 but not laterally. The recess 40 prevents lateral transmission of afterglow light. Then the recessed location of the PMT 12 face would keep any lateral light from striking the PMT face in any event. Accordingly, afterglow light from one or more ,ells can generate only some level of diffused lighting in the space between sample holder plate 30 and the baffle 60. The black surface of plate body 35, of baffle 60, and of the focussing collar 64 absorb light, attenuating the afterglow so that even diffused (reflected) light cannot strike the PMT face.

The space overhead of the microtiter plate also contains diffused light. Some emitted light from the sample being assayed and afterglow from the previously assayed sample(s) is directed upward into this space. The black surface of the plate body 35 and of the upper shelf 29 and the inside of housing 100 attenuate any such afterglow so that afterglow light in the overhead space is not believed to generate false PMT readings.

As an aside, it should be appreciated that the foregoing discussion of afterglow light applies as much to the initial luminescence or preglow when an assay reaction involves delay and appropriately injector 14 is not in line of sight with PMT 12.

An (optional) expedient contemplated herein to increase the quantity of signal light transmitted by a sample being assayed is to provide a reflector 126 in line with PMT 12, e.g., around injector nozzle 13. Reflector 126 acts to reflect back the light emitted upwardly from the sample being assayed. In addition, the reflector shields the line of sight well from reflected afterglow light from adjacent wells.

It may be noted that the combination of a black plate body 35 and optically clear cups (for wells 30) may not always be desired. Although black is strongly preferred for body 35, the side wall of wells 30 need not be transparent. An alternative construction contemplated by the inventors hereof employs a white or other reflective coating, e.g., mirror coating, on the side wall of each well 30. A comparative study between wells with transparent side walls and wells with a white (reflective) side wall demonstrated that wells with the reflective side wall transmitted nearly double the luminescence signal.

We claim:
1. A luminometer comprising:
(a) a movable table adapted for positioning thereon of at least one opaque sample holder plate characterized by having a multiplicity of sample wells in rows and columns and by each sample well having a transparent bottom wall;
(b) at least one stationary reagent injector nozzle positioned above said table;
(c) at least one stationary light detector positioned beneath said table, said reagent injector nozzle and light detector being in line of sight registry;
(d) an X-Y movement mechanism operatively connected to said table to move said table and a sample holder plate positioned on said table so that one by one every sample well on a said plate can be interposed into the line of sight registry of said reagent injector nozzle with said light detector whereby a burst of luminescence generated in the sample well within the line of sight registry of said injector nozzle and said light detector may be received by said light detector to be a luminescence assay;
(e) means for preventing light emitted from any sample well not in line of sight registry with said light detector from impinging therein; and
(f) means for generating and displaying and/or recording a signal that is in a predetermined proportion to the intensity of the detected luminescence as the output signal assay results from said light detector.

2. The luminometer of claim 1 further comprising a baffle plate between said table and said light detector, said baffle plate being provided with an aperture therein wherein said light detector is disposed, the baffle plate and table being located one relative to the other so that at each assay registry only a single sample well on a sample holder plate positioned on said table can be in line of sight to said light detector.

3. The luminometer of claim 2 further comprising an iris located in said aperture on the baffle plate, the iris being located between light detector and table, said iris limiting the maximum width line of sight path from a sample well to said light detector to less than the diameter of the sample well.

4. The luminometer of claim 1 further comprising a reflector above said sample holder in line of sight above said light detector, whereby luminescence emitted up from the sample well on said plate that is in line of sight to said light detector will be reflected back down through said sample.

5. The luminometer of claim 1 wherein the light detector comprises a photo multiplier tube.

6. The luminometer of claim 1 wherein the means for preventing light from any sample well not in line of sight with said light detector from impinging thereon comprises a black surface absorptive of light on the internal surface of said luminometer.

7. The luminometer of claim 1 wherein said movable table is adapted to position thereon three sample holder plates; and wherein three nozzles and three light detectors are present, whereby three samples may be assayed at the same time.

* * * * *